US007229636B1

(12) United States Patent
Quay et al.

(10) Patent No.: US 7,229,636 B1
(45) Date of Patent: Jun. 12, 2007

(54) CYANOCOBALAMIN LOW VISCOSITY AQUEOUS FORMULATIONS FOR INTRANASAL DELIVERY

(75) Inventors: Steven C. Quay, Edmonds, WA (US); Peter C. Aprile, East Northport, NY (US); Zenaida O. Go, Clifton, NJ (US); Anthony P. Sileno, Brookhaven Hamlet, NY (US)

(73) Assignee: Nastech Pharmaceutical Company Inc., Bothell, WA (US)

( * ) Notice: Subject to any disclaimer, the term of this patent is extended or adjusted under 35 U.S.C. 154(b) by 157 days.

(21) Appl. No.: 10/787,385

(22) Filed: Feb. 26, 2004

Related U.S. Application Data

(60) Provisional application No. 60/451,899, filed on Mar. 4, 2003, provisional application No. 60/461,583, filed on Apr. 8, 2003, provisional application No. 60/474, 204, filed on May 29, 2003.

(51) Int. Cl.
*A61F 13/00* (2006.01)

(52) U.S. Cl. ....................... 424/434; 424/1.73; 514/52; 435/86; 536/26.4

(58) Field of Classification Search .................. 514/52; 424/1.73, 434; 435/86; 536/26.4
See application file for complete search history.

(56) References Cited

U.S. PATENT DOCUMENTS 2,703,302 A 3/1955 Rickes et al.
2,703,303 A 3/1955 Rickes et al.
2,746,796 A 5/1956 Germain
2,914,222 A 11/1959 Meshberg
2,951,017 A 8/1960 Speedie et al.
3,000,793 A 9/1961 McDaniel
3,018,225 A 1/1962 Long
3,057,851 A 10/1962 Melle
3,120,508 A 2/1964 Bernhauer et al.
3,282,781 A 11/1966 Macek et al.
3,548,057 A 12/1970 Kelley et al.
3,577,537 A 5/1971 Howe et al.
3,584,115 A 6/1971 Gebhart et al.
3,957,968 A 5/1976 Valan
4,174,295 A 11/1979 Bargigia et al.
4,525,341 A 6/1985 Deihl
4,724,231 A * 2/1988 Wenig ......................... 514/52
4,727,231 A 2/1988 Weng
5,797,390 A 8/1998 McSoley
5,801,161 A 9/1998 Merkus
5,825,625 A 10/1998 Esterberg et al.
6,685,421 B1 2/2004 Farina

FOREIGN PATENT DOCUMENTS

| | | |
|---|---|---|
| CA | 1317881 | 5/1993 |
| EP | 0131315 A2 | 2/1984 |
| EP | 0130550 A2 | 6/1984 |
| WO | WO 86-05987 | 10/1986 |
| WO | WO 86/05988 | 10/1986 |

OTHER PUBLICATIONS

Garcia-Arieta et al. Spray-Dried Powders as Nasal Absorption Enhancers of Cyanocobalamin., Dec. 2001., Biol. Pharm. Bull. 24(12) pp. 1411-1416.*

Slot et al. Normalization of Plasma Vitamin B12 Concentration by Intranasal Hydroxocobalamin in Vitamin B12 -Deficient Patients., (1997)., Gastroenterology 1997(113) pp. 430-433.*

U.S Department of Health and Human Services, (Draft) Guidance for Industry, Bioavailability and Bioequivalence Studies for Nasal Aerosols and Nasal Sprays for Local Action, Apr. 2003, pp. 1-36+ attachments, U.S. Food and Drug Administration, Center for Drug Evaluation and Research, Biopharmaceutics.

Raymond W. Monto, John W. Rebuck, Michael Brennan, Crystalline $B^{12}$ Inhallation Theraphy in Perniciouos Anemia, The American Journal of the Medical Sciences, Feb. 1953, pp. 113-119, Publisher: Division of Hematology and the Department of Laboratories, The Henry Ford Hospital, Detroit, Michicagn Published in: Detroit, MI, US.

(Continued)

*Primary Examiner*—James O. Wilson
*Assistant Examiner*—Paul V. Ward
(74) *Attorney, Agent, or Firm*—Peter J. Knudsen

(57) ABSTRACT

A stable pharmaceutical mercury-free aqueous solution of cyanocobalamin comprised of cyanocobalamin and water wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin with the proviso that the solution is essentially free of mercury and mercury-containing compounds. The present invention is also directed towards a method for elevating the vitamin B12 levels in the cerebral spinal fluid (CSF) comprising administering intranasally a sufficient amount of a mercury-free cyanocobalamin solution so as to increase the average ratio of vitamin B12 in the CSF to that in the blood serum (B12 CSF/B12 Serum×100) to at least about 1.1 comprising intranasally administering an aqueous solution of a cyanocobalamin, wherein said solution of cyanocobalamin has a bioavailability of at least 7% relative to an intramuscular injection of a cyanocobalamin.

31 Claims, No Drawings

OTHER PUBLICATIONS

Raymond W. Monto, John W. Rebuck, Nasal Instiliation and Inhalation of Crystalline Vitimin $B^{12}$ in Pernicious Anemia, A.M.A. Archives 6 Internal Medicine, vol. 93, 1954, From the Division of Hematology (Dr. Monto) and the Department of Laboratories (Dr. Rebuck), The Henry Ford Hospital. Pages 219-230. Detroit, MI, US.
Raymond W. Monto, John W. Rebuck, Observations on the Mechanism of Intranasal Absorption of Vitamin $B^{12}$ in Pernicious Anemia. Blood, vol. 10, 1955, pp. 1151-1155, From the Division of Hematology (Dr. Monto) and the Department of Laboratories (Dr. Rebuck), The Henry Ford Hosptial. Detroit, MI, US.
A. Killander and I. Werner, Studies on Maintenance Treatment of Penicious Anaemia, Vitamin $B^{12}$ and Intrinsic Factor Europaisches Symposian Hamburg, 1961, pp. 663-667, Ed. H.c. Heinrich, Enke, Stuttgart, Department of Pediatris and Internal Medicine, Akademiska, Sjukhuset, Uppsala, Sweden.
N.K. Shinton and A.K. Singh, Vitamin $B^{12}$ Absorption by Inhalation, Chemical Abstracts, vol. 66, No. 15, Coden: Chaba8, The American Chemical Society, Apr. 10, 1967, p. 6024, Abstract 64246(e) Northampton Sts, Easton, PA, US.
N.K. Shinton and A.K. Singh, Vitamin $B^{12}$ absorption by inhalation, Brit. J. Haemat, 1967, 13. pp. 75-79, Department of Haematology, Coventry and Warwickshire Hospital, Coventry.
Forest Laboratories, Inc., Long Acting oral carrier, Chemical Abstracts, vol. 77, Year 1972, p. 263, Abstract 105623(y).
Sally Mathison, Rakesh Nagilla, and Uday B. Kompella, Nasel Route for Direct delivery of Solutes to the Central Nervous System: Fact or Fiction? Journal of Drug Targeting, 1998, vol. 5, No. 6, pp. 415-441 Departement of Pharmacal Sciense, Department of Chemistry, Auburn University, Auburn, AL US.
Anthony J. Cutie and John J. Sciarra, Intranasal Pharmaceutical Aerosols, Aerosal Age, The International authority in Spray Packaging, Aerosol Age Magazine, Oct. 1982, pp. 1-4.
R.K. Chandra, Gloria Heresi, and G. Woodford, Double-blind controlled crossover trial of 4% intranasal sodium cromoglycate solution in patients with seasonal allergic rhinitis, Annals of Allergy, Sep. 1982, vol. 49, From the Department of Pediatrics, Memorial University of Newfoundland, Janeway Child Health Ceneter and Health Sciences Center, St. John's , Newfoundland, Canada.
Edited by James E.F. Reynolds, Cyanocobalamin, Martindale, The Extra Pharmacopoeia, 1982, Abstract 7853-d, and Page 1645, Cyanocobalamin Injection, 28th Edition, Published by direction of the Council of The Pharmaceutical Society of Great Britain and prepared in the Society's Department of Pharmaceutical Sciences, The Pharmaceutical Press, London, UK.
Cheng Der Yu, Richard Jones, Jim Wright, and Maida Henesian, Characterization of dose delivery and spray pattern of a metered-dose flunisolide nasel spray, Drug development and Industrial Pharmacy, 1983, 9(3), pp. 473-483, Institute of Pharmaceutical Sciences, Syntex Research, Palo Alto, CA Marcel Dekker, Inc., US.
Anwar A. Hussain, Yukihiko Aramaki, Studies on the Intranasal Absorption of vitamin $B^{12}$ in the Rat, Final Report, Dec. 1984, University of Kentucky, College of Pharmacy, Lexington, KY, US.
Valois, Pumps for Pharmacy, Year Unknown (product brochure).
John J. Siarra, Aerosols, Chapter 92, Year Unknown, pp. 1614-1621, Arnold & Marie Schwartz Collet of Pharmacy and Health Science, Long Island Univeristy, Brooklyn, NY, US.
T.Q.Nijst, R.A. Wevers, H.C. Schoonderwaldt, O.R. Hommes, A.F.J. De Haan, Vitamin B12 and folate concentrations in serum and cerebrospinal fluid of neurological patients with special reference to multiple sclerosis and dementia, Journal of Neurology, Neurosugery, and Psychiatry, Year 1990; 53, pp. 951-954.
Garcia-Arieta, A.; Torrado-Santiago, S.; Goya, L.; Torrado, J. J, . Spray-dried powers as nasal absorption enhancers of cyanocobalamin, Biol.Pharm.Bull, date- 2001, vol. 24, issue- 12, pp. 1411-1416, Pharmaceutical Society of Japan.
U.S. Department of Health and Humans Services, Guidance for Industry, Nasal spary and inhalation solution, suspension, and spray drug products-chemistry, manufacturing, and controls documentation, Jul. 2002, pp. 1-44, Food and Drug Administration, Center for Drug Evaluation and Research, Rockville, MD, US.

* cited by examiner

CYANOCOBALAMIN LOW VISCOSITY AQUEOUS FORMULATIONS FOR INTRANASAL DELIVERY

This claims priority under 35 U.S.C. §119 (e) to U.S. Provisional Application No. 60/451,899 filed Mar. 4, 2003; U.S. Provisional Application No. 60/461,583 filed Apr. 8, 2003, and U.S. Provisional Application No. 60/474,204 filed May 29, 2003, the entire contents of which are incorporated herein by reference

BACKGROUND OF THE INVENTION

Vitamin B12 is a dietary essential, a deficiency of which results in defective synthesis of DNA in any cell in which chromosomal replication and division are taking place. Since tissues with the greatest rate of cell turnover show the most dramatic changes, the hematopoietic system is especially sensitive to vitamin B12 deficiencies. An early sign of B12 deficiency is a megaloblastic anemia. Dietary B12, in the presence of gastric acid and pancreatic proteases, is released from food and salivary binding protein and bound to gastric intrinsic factor. When the vitamin B12-intrinsic factor complex reaches the ileum, it interacts with a receptor on the mucosal cell surface and is actively transported into circulation. Adequate intrinsic factor, bile and sodium bicarbonate (suitable pH) all are required for ileal transport of vitamin B12. Vitamin B12 deficiency in adults is rarely the result of a deficient diet; rather, it usually reflects a defect in one or another aspect of this complex sequence of absorption. Achlorhydria and decreased secretion of intrinsic factor by parietal cells secondary to gastric atrophy or gastric surgery is a common cause of vitamin B12 deficiency in adults. Antibodies to parietal cells or intrinsic factor complex also can play a prominent role in producing deficiency. A number of intestinal diseases can interfere with absorption. Vitamin B12 malabsorption is seen with pancreatic disorders (loss of pancreatic protease secretion), bacterial overgrowth, intestinal parasites, sprue, and localized damage to ileal mucosal cells by disease or as a result of surgery. The recommended daily intake of vitamin B12 in adults is 2.4 μg.

There are four main forms of vitamin $B_{12}$: cyanocobalamin: hydroxocobalamin, methylcobalamin and adenosylcobalamin. Methylcobalamin and adenosylcobalamin are unstable and damaged by light. They are therefore unsuitable for use in dietary supplements or pharmaceuticals and are not essential since they can be formed from cyanocobalamin or hydroxocobalamin within the body. The main form of vitamin $B_{12}$ found in food is hydroxocobalamin. The main form used therapeutically and in nutritional supplements is cyanocobalamin, chosen because it is the most stable form and therefore easiest to synthesize and formulate.

Because deficiencies of vitamin B12 are generally caused by the inability of the vitamin to be absorbed in the small intestine due to a breakdown in the vitamin B12-intrinsic factor complex transport mechanism, vitamin B12 must therefore be administered systemically. Currently, therapeutic amounts of cyanocobalamin are administered by intramuscular or deep subcutaneous injection of cyanocobalamin. However, patients must return to the physician's office periodically to receive additional injections to maintain their levels of vitamin B12. However, an intranasal gel cyanocobalamin preparation, NASCOBAL® is currently being marketed in which cyanocobalamin is administered intranasally as maintenance vitamin B12 therapy. However, many patients find the consistency of the intranasal gel unpleasant and would prefer to have administered intranasally a low viscosity spray containing cyanocobalamin.

The prior art suggests that for vitamin B12 to be absorbed intranasally in therapeutically beneficial amounts, the concentration of the B12 in solution must either be greater that 1% by weight, see Merkus, U.S. Pat. No. 5,801,161 or be administered intranasally in a viscous gel, Wenig, U.S. Pat. No. 4,724,231 so that the gel remains in the nostril for an extended period of time. In fact Wenig states that B12 administered intranasally in a low viscosity solution is not in contact with the nasal mucosa long enough for a sufficient period of time to permit useful absorption. Wenig claims that most of the B12 is wasted if the solution has a low viscosity. Merkus developed intranasal formulations of hydroxocobalamin having a concentration of hydroxocobalamin greater than 1%, however hydroxocobalamin is not very stable and thus has a short shelve-life. Merkus chose hydroxocobalamin because cyanocobalamin is not soluble in an aqueous solution at concentrations greater than 1%.

U.S. Pat. No. 4,525,341, Deihl, discloses a method of administering vitamins intranasally but do not enable a specific formulation containing only cyanocobalamin. International Patent Application No. PCT/US86/00665, publication no. WO 86/05987, and European Patent Application No. EP0218679B1, discloses nasal spray composition containing vitamin $B_{12}$ as cyanocobalamin. However, the specific spray formulations all contained a mercury compound as a preservative, however the disclosure did require the presence of mercury compounds. Other preservatives were also mentioned including benzalkonium chloride and chlorobutanol. As was stated above, an intranasal gel containing cyanocobalamin, NASCOBAL®, is currently being produced and marketed by Nastech Pharmaceutical Company Inc. of Bothell, Wash. It is very effective in maintaining levels of vitamin B12 for patients who have been deficient in the past but have recovered their levels of B12 through intramuscular injections. However, a number of patients find the consistency of the gel unpleasant in their nose, and would prefer an intranasal formulation that has a lower viscosity and is free of mercury compounds. Thus, there is a need to produce a pharmaceutically stable aqueous solution of cyanocobalamin that has a low viscosity, is free of mercury compounds and has sufficient bioavailability to be used as a maintenance therapy for vitamin B12.

SUMMARY OF THE INVENTION

The present invention fills this need by providing for a stable pharmaceutical solution of cyanocobalamin suitable for intranasal administration, having a viscosity less than about 1000 cPs, wherein said intranasal solution of cyanocobalamin has a bioavailability of at least 7% of the bioavailability of an intramuscular injection of cyanocobalamin and is free of mercury compounds.

A preferred formulation is comprised of cyanocobalamin, citric acid, sodium citrate, and water wherein the viscosity is less than 1000 cPs, and wherein the solution of cyanocobalamin has a bioavailability of at least 8%, more preferably at least about 9, 10, 11, or 12% of the bioavailability of an intramuscular injection of cyanocobalamin.

Preferred compositions within the scope of this invention will contain a humectant to inhibit drying of the mucous membranes and to prevent irritation. Any of a variety of humectants can be used including but not limited to sorbitol, propylene glycol or glycerol. A preferred humectant is glycerin.

A preservative is generally employed to increase the shelf life of the compositions. Examples of preservative include but are not limited to benzyl alcohol, chlorobutanol and benzalkonium chloride. A preferred preservative is benzalkonium chloride. A suitable concentration of the preservative will be from 0.002% to 2.0% based upon the total weight, although there may be appreciable variation depending upon the agent selected.

A most preferred formulation has the concentration of cyanocobalamin at 0.5% (percent of total weight), citric acid 0.12%, sodium citrate 0.32%, glycerin 2.23%, benzalkonium chloride 0.02% and 96.79% water.

Another embodiment of the present invention is a method for administering cyanocobalamin comprised of infusing the nose with an aqueous solution of cyanocobalamin, wherein the solution of cyanocobalamin has a viscosity of less than 1000 cPs, and wherein said solution of cyanocobalamin has a bioavailability of at least about 7% relative to an intramuscular injection of cyanocobalamin. Preferably, the bioavailability is at least 8%, 9%, 11% or 12%.

The present invention is further directed towards a method for elevating the vitamin B12 levels in the cerebral spinal fluid (CSF) comprising intranasally administering a solution of cyanocobalamin so as to increase the average ratio of vitamin B12 in the CSF to that in the blood serum (B12 CSF/B12 Serum×100) to at least about 1.1, wherein said solution of cyanocobalamin has a bioavailability of at least 7% relative to an intramuscular injection of cyanocobalamin. In a more preferred embodiment the B12 CSF levels are increased so that the ratio of B12 in the CSF to the levels in the blood serum is at least 1.9.

DETAILED DESCRIPTION OF THE INVENTION

The following definitions may aid in the understanding of the present invention.

"About": is taken to be a relative term denoting an approximation of plus or minus 20% of the nominal value it refers to. For the field of pharmacology and clinical medicine and analogous arts that are the subject of this disclosure, this level of approximation is appropriate unless the value is specifically stated to be critical or to require a tighter range.

"Nasal mucosa": the nasal mucosa is taken to be the lining of the vestibule of the nose, where vascularized, and extending interiorly to the boundaries of the oropharynx and sinuses.

"Aqueous": refers to a solution formed in water, but may contain lesser amounts of other co-solvents.

"Bioavailability" is defined as the rate and extent to which the active ingredient or active moiety is absorbed from a drug product and becomes available at the site of action, [21 CFR §320.1(a)].

"Bioavailability of the intranasal spray relative to an intramuscular injection of cyanocobalamin" means the percent amount a dose of the intranasal taken up by the systemic vascular system in comparison to the same amount of cyanocobalamin injected. For example, assuming an intramuscular injection of a solution of cyanocobalamin containing 100 μg of cyanocobalamin would have a 100% bioavailability, if an intranasal dose of cyanocobalamin contains 100 μg and has at least 7% bioavailability relative to an injection of cyanocobalamin, at least 7 μg of cyanocobalamin would be taken up into the blood vasculature. Likewise, if the intranasal dose of cyanocobalamin contained 500 μg, at least 35 μg of cyanocobalamin would be taken up into the blood vasculature, if the intranasal formulation had a bioavailability of at least 7%.

"Stability": during storage, any compositional change measured in a parameter, examples of which include but are not limited to concentration, degradation, viscosity, pH, or particle size, that is considered to significantly affect the quality attributes of the product over time, denotes instability. In a similar vein, changes that are not considered to significantly affect the quality attributes of the product connote stability. The time period over which stability is measured is relative depending on the intended utility of the composition. Accelerated stability at higher temperature is sometimes taken as a more speedy way of extrapolating stability over longer periods of time than are actually measured.

"Pharmaceutically acceptable": refers to a composition which when administered to a human or a mammal by the indicated route of administration, provokes no adverse reaction which is disproportionate to the benefit gained by administration of said compound.

"Mammal" shall include any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits. "Patient" or "subject" is used herein interchangeably with "mammal."

"Intranasal delivery" shall mean delivery of a drug primarily via the mucosa of the nasal cavity. This includes the superior, middle and inferior nasal turbinates and the nasal pharynx. Note that the olfactory region is concentrated in the superior (upper ⅓) of the nasal turbinates. Cilial action pushes material back toward the oropharynx, so material deposited in the nasal vestibule encounters the nasal mucosa before entering the throat.

"Substantially free" refers to the level of a particular active ingredient in the compositions of the invention, wherein the particular active ingredient constitutes less than 20%, preferably less than 10%, more preferably less than 5%, and most preferably less than 1%, by weight based on the total weight of active ingredients in the composition.

Delivery vehicles herein found useful include actuator dispensers commonly used for nasal solutions and gels. Embodiments of this technology include multiple, single-dose, metered dose, child resistant, and disposable dispensers, and their kits.

As used herein "peak concentration ($C_{max}$) of cyanocobalamin in a blood plasma", "area under concentration vs. time curve (AUC) of cyanocobalamin in a blood plasma", "time to maximal plasma concentration ($t_{max}$) of vitamin in a blood plasma" are pharmacokinetic parameters known to one skilled in the art. [Laursen et al., *Eur. J. Endocrinology,* 135: 309-315, (1996)]. The "concentration vs. time curve" measures the concentration of cyanocobalamin in a blood serum of a subject vs. time after administration of a dosage of cyanocobalamin to the subject either by intranasal, subcutaneous, or other parenteral route of administration. "$C_{max}$" is the maximum concentration of cyanocobalamin in the blood serum of a subject following a single dosage of cyanocobalamin to the subject. The term "$t_{max}$" is the time to reach maximum concentration of cyanocobalamin in a blood serum of a subject following administration of a single dosage of cyanocobalamin to the subject.

As used herein, "area under concentration vs. time curve (AUC) of cyanocobalamin in a blood plasma" is calculated according to the linear trapezoidal rule and with addition of the residual areas. A decrease of 23% or an increase of 30% between two dosages would be detected with a probability of 90% (type II error $\beta$=10%). The "delivery rate" or "rate of absorption" is estimated by comparison of the time ($t_{max}$) to reach the maximum concentration ($C_{max}$). Both $C_{max}$ and $t_{max}$ are analyzed using non-parametric methods. Comparisons of the pharmacokinetics of subcutaneous, intravenous and intranasal cyanocobalamin administrations were performed by analysis of variance (ANOVA). For pair wise comparisons a Bonferroni-Holmes sequential procedure was used to evaluate significance. The dose-response relationship between the three nasal doses was estimated by regression analysis. $P<0.05$ was considered significant. Results are given as mean values +/−SEM. (Laursen et al., 1996.)

As noted above, the present invention provides improved methods and compositions for intranasal delivery cyanocobalamin to mammalian subjects for treatment or prevention of a variety of diseases, disorders and conditions. Examples of appropriate mammalian subjects for treatment and prophylaxis according to the methods of the invention include, but are not restricted to, humans and non-human primates, livestock species, such as horses, cattle, sheep, and goats, and research and domestic species, including dogs, cats, mice, rats, guinea pigs, and rabbits.

An initial therapy, the patient should receive daily intramuscular injections of 100 μg of cyanocobalamin for about 1 to 2 weeks, together with 1 to 5 mg of folic acid. Intramuscular injections of cyanocobalamin should not be greater than 100 μg as doses in excess of 100 μg are rapidly cleared from the plasma into the urine, and administration of larger amounts of vitamin B12 will not result in greater retention of larger amounts of the vitamin.

The cyanocobalamin nasal spray of the present invention is directed towards the maintenance of the hematological status of patients who are in remission following intramuscular vitamin B12 therapy. So instead of a once a month injection of 100 μg of cyanocobalamin, using the cyanocobalamin spray, the patient self-administers a dose of the nasal spray of the present invention containing 500 μg of cyanocobalamin once or twice a week. The maintenance therapy of the intranasal cyanocobalamin is for any patient that had been diagnosed with a vitamin B12 deficiency, but especially for those treated for pernicious anemia and dietary deficiency of vitamin B12 occurring in strict vegetarians, the so-called vegans who eat no animal products. Maintenance cyanocobalamin therapy using the cyanocobalamin solution of the present invention is also indicated for those afflicted with malabsorption of vitamin B12 resulting from structural or functional damage to the stomach, where intrinsic factor is secreted or to the ileum, where intrinsic factor facilitates B12 absorption. These conditions include tropical sprue and nontropical sprue (Idiopathic steatorrhea, gluten-induced enteropathy).

Maintenance cyanocobalamin therapy using the cyanocobalamin solution of the present invention is also indicated for those afflicted with malabsorption of vitamin B12 resulting from inadequate secretion of intrinsic factor, resulting from lesion that destroys the gastric mucosa (ingestion of corrosives, extensive neoplasia), and a number of conditions associated with a variable degree of gastric atrophy (such as multiple sclerosis, human immunodeficiency viral (HIV) infection certain endocrine disorders, iron deficiency, and subtotal gastrectomy). Structural lesions that lead to B12 deficiency include ileitis, ileal resections, Crohn's disease and malignancies. Vitamin B12 deficiencies may also be the result of competition by intestinal parasites, and inadequate utilization of vitamin B12 occurring if antimetabolites for the vitamin are employed in the treatment of neoplasia.

The intranasal cyanocobalamin solution of the present invention can also be used for individual who require above normal levels of vitamin B12, due to for example pregnancy, thyrotoxicosis, hemolytic anemia, hemorrhage, malignancy, hepatic and renal disease.

As was stated above, the present invention provides for a stable pharmaceutical solution of cyanocobalamin suitable for intranasal administration, having a viscosity less than about 1000 cPs, wherein said intranasal solution of cyanocobalamin has when administered intranasally a bioavailability of at least 7% of the bioavailability of an intramuscular injection of cyanocobalamin. The intranasal formulation will generally be comprised of in addition to water and cyanocobalamin, a buffering agent to maintain the pH between 4 and 6 preferably about 5, a humectanct to inhibit drying of the mucous membranes and a preservative.

A preferred formulation is comprised of cyanocobalamin, citric acid, sodium citrate, and water wherein the viscosity is less than 1000 cPs, and wherein the solution of cyanocobalamin has a bioavailability of at least 7%, more preferably at least about 8, 9, 10, 11, 12% or more of the bioavailability of an intramuscular injection of cyanocobalamin.

Preferred compositions within the scope of this invention will contain a humectant to inhibit drying of the mucous membranes and to prevent irritation. Any of a variety of humectants can be used including, for example sorbitol, propylene glycol or glycerol. A preferred humectant is glycerin.

A preservative is generally employed to increase the shelf life of the compositions. Examples of preservative include benzyl alcohol, parabens thimerosal, chlorobutanol, benzethonium chloride and benzalkonium chloride. A preferred preservative is benzalkonium chloride. A suitable concentration of the preservative will be from 0.002% to 2% based upon the total weight, although there may be appreciable variation depending upon the agent selected.

A most preferred formulation has the concentration of cyanocobalamin at 0.5% (percent of total weight), citric acid 0.12%, sodium citrate 0.32%, glycerin 2.23%, benzalkonium chloride solution 0.02% and 96.79% water.

Other buffering agent combination include but are not limited to:

Monopotassium phosphate and disodium phosphate,

Potassium biphthalate and sodium hydroxide, and

Sodium acetate and acetic acid.

Another embodiment of the present invention is a method for administering cyanocobalamin comprised of infusing the nose with an aqueous solution of cyanocobalamin, wherein the solution of cyanocobalamin has a viscosity of less than 1000 cPs, and wherein said solution of cyanocobalamin has a bioavailability of at least 7% relative to an intramuscular injection of cyanocobalamin. Preferably the bioavailability is at least about 8, 9, 10, 11, 12% or more of the bioavailability of an intramuscular injection of cyanocobalamin.

The present invention is further directed towards a method for elevating the vitamin B12 levels in the cerebral spinal fluid (CSF) comprising intranasally administering a solution of cyanocobalamin so as to increase the average ratio of vitamin B12 in the CSF to that in the blood serum (B12 CSF/B12 Serum×100) to at least about 1.1, wherein said solution of cyanocobalamin has a bioavailability of at least 7% relative to an intramuscular injection of a cyanocobalamin. In a more preferred embodiment the B12 CSF levels are increased so that the ratio of B12 in the CSF to the levels in the blood serum is at least 1.9.

This is a significant embodiment of the present invention because vitamin B12 deficiency can result in irreversible damage to the nervous system. Progressive swelling of myelinated neurons, demyelination, and neuronal cell death are seen in the spinal column and cerebral cortex. This causes a wide range of neurological signs and symptoms, including paresthesias of the hands and feet, diminution of vibration and position senses with resultant unsteadiness, decreased deep tendon reflexes, and, in the later stages, confusion, moodiness, loss of memory, and even a loss of central vision. The patient may exhibit delusions, hallucinations, or even an overt psychosis. Since the neurological damage can be dissociated from the changes in the hematopoietic, vitamin B12 deficiency must be considered as a possibility in elderly patients with dementia and psychiatric disorders, even if they are not anemic. Thus, the embodiment of the present invention directed towards increasing the level of vitamin B12 in the CSF can have tremendous benefit for neurological patients. Thus, intranasal administration of vitamin B12 can be used to treat such diseases as Alzheimer's disease, dementia, and multiple sclerosis.

Preferred formulations are the following:

Cyanocobalmin Nasal Spray 500 mcg/0.1 mL

Formulation:

| Component | Current Nasal Solution Quantity (% w/w) |
|---|---|
| Cyanocobalamin, USP | 0.50 |
| Citric acid anhydrous, USP | 0.12 |
| Sodium citrate dihydrate, USP | 0.32 |
| Glycerin, USP | 2.23 |
| Benzalkonium chloride (50%), NF | 0.04 |
| Purified water q.s. | 100.0 |

Alternative buffer systems and amounts that can be used for Cyanocobalamin Nasal Spray

| | Quantity (% w/w) |
|---|---|
| 1) Citric Acid-Phosphate buffer | |
| Citric Acid anhydrous, USP | 0.240 |
| Dibasic Sodium Phosphate anhydrous | 0.357 |
| 2) Acetate buffer | |
| Sodium Acetate anhydrous, USP | 0.220 |
| Acetic Acid, glacial, USP | 0.064 |
| 3) Phosphate buffer | |
| Monobasic Potassium Phosphate anhydrous, NF | 0.483 |
| Dibasic Sodium Phosphate anhydrous | 0.004 |

The intranasal formulations of the present invention can be administered using any spray bottle or syringe. A preferred nasal spray bottle is the, "Nasal Spray Pump w/Safety Clip, Pfeiffer SAP #60548, which delivers a dose of 0.1 mL per squirt and has a diptube length of 36.05 mm. It can be purchased from Pfeiffer of America of Princeton, N.J.

The following examples are provided by way of illustration, not limitation.

EXAMPLE 1

Comparison of Intranasal Cyanocobalamin Solution of the Present Invention with NASCOBAL® and Intramuscular Injections of Cyanocobalamin Introduction Nascobal® (Cyanocobalamin, USP) is a synthetic form of vitamin $B_{12}$ with equivalent vitamin $B_{12}$ activity. The chemical name is 5,6-dimethyl-benzimidazolyl cyanocobamide. Currently, Nascobal® (Cyanocobalamin, USP) is marketed as a self-administered nasal gel. The recommended dose of Nascobal® (Cyanocobalamin, USP) in subjects with vitamin $B_{12}$ malabsorption who are in remission following inject able vitamin $B_{12}$ therapy is 500-μg administered intranasally once weekly.

Vitamin $B_{12}$ deficiency has a number of causes, including malabsorption of vitamin $B_{12}$ resulting from structural or functional damage to the gastrointestinal system and dietary deficiency of vitamin $B_{12}$.

The purposes of this study are to compare the bioequivalence of vitamin B12 nasal gel versus the nasal spray, and to evaluate the relative bioavailability of three preparations of vitamin B12 in a fasted state in normal healthy male and female subjects.

Intranasal cyanocobalamin gel is approved for a dose of 500 μg. The current study also utilizes a cyanocobalamin nasal spray at the same 500 μg dose and an intramuscular dose of 100 μg.

Study Objectives

To compare the pharmacokinetic profile of a single intranasally-administered spray, single intranasally-administered gel (Nascobal®), and single intramuscular-administered vitamin $B_{12}$ in a fasted state in normal healthy male and female subjects.

Investigational Plan

Overall Study Design and Plan

This study was a single-site, open-label, 3-way (3-treatment, 6-sequence) crossover, pharmacokinetic study of vitamin $B_{12}$ administered via intranasal (IN) spray (500-μg), IN gel (Nascobal®) (500-μg), and intramuscular (IM) injection (100-μg) in fasted normal healthy male and female subjects, as follows:

Treatment A: One IN spray administration of 500-μg vitamin $B_{12}$. The intranasal formulation was comprised of a preferred embodiment of the present invention and contained cyanocobalamin at a concentration of 0.5% (percent of total weight), citric acid 0.12%, sodium citrate 0.32%, glycerin 2.23%, 50% benzalkonium chloride solution 0.04% and 96.79% water.

Treatment B: One IN gel administration of 500-μg vitamin $B_{12}$ (Nascobal®).

Treatment C: One IM administration of 100-μg vitamin $B_{12}$.

Subjects were on a Vitamin $B_{12}$-free diet throughout each confinement period. Subsequent treatments will be dosed no sooner than 14 days following the preceding treatment dose administration.

Treatments

Treatments Administered

On Day 1 of Periods I, II, and III after an 8 hour fast, subjects received a single IN spray of 500-µg vitamin $B_{12}$ (Treatment A), a single IN gel of 500-µg vitamin $B_{12}$ (Nascobal®) (Treatment B), or a single IM administration of 100-µg vitamin $B_{12}$ (Treatment C) based upon a randomization generated by the PPD Development Biostatistician in one of six sequences. Following all periods, all subjects were to have received each treatment in a crossover manner. A washout period of 14 days separated the three dosing periods.

On the morning of Day 1, subjects assigned to Treatment A received a single IN spray administration of 500 µg of vitamin $B_{12}$. Subjects assigned to Treatment B received a single IN gel administration of 500 µg of vitamin $B_{12}$ (Nascobal®). Subjects assigned to Treatment C received a single IM administration of 100 µg of vitamin $B_{12}$. Doses were preceded by an overnight fast (i.e., at least 8 hours) from food (not including water) and were followed by a fast from food (not including water) for at least 4 hours post-dose.

While confined at the clinical site, subjects received a standardized vitamin $B_{12}$-deficient diet at scheduled times which did not conflict with other study-related activities. A registered dietician set up the diet, and the food staff maintained a diet diary. No dietary supplements were permitted during the study. Subjects abstained from consuming alcohol-containing, grapefruit-containing, or caffeine-containing foods or beverages for 72 hours prior to Check-in.

Study Variables

For each subject, the following pharmacokinetic parameters were calculated whenever possible, based on the serum concentrations of vitamin $B_{12}$ from Treatments A, B, and C according to the model independent approach: $C_{max}$, $T_{max}$, and $AUC_{0-t}$ Pharmacokinetic Measurements Blood samples for PK analysis of vitamin $B_{12}$ levels were collected via an indwelling catheter and/or via direct venipuncture using 5-mL yellow-top Vacutainer® Hemogard™ evacuated serum separator collection tube. Blood samples for PK analysis of vitamin $B_{12}$ levels were collected on Day −1 at 0, 6, and 12 hours and Day 1 at 0 hour (i.e., pre-dose); 30 minutes; 1, 1.5, 2, 4, 6, 8, 10, 12, 18, 24, 36, 48, 60, 72, 84 and 96 hours post-dose during each period.

Appropriateness of Measurements

The pharmacokinetic parameters used in this study were those typically used to assess bioequivalence. All assessments of bioequivalence were based on comparisons of $AUC_{0-t}$, $T_{max}$, and $C_{max}$ (test versus reference treatments).

AUC is a measure of the extent of drug bioavailability and reflects the total amount of drug that reaches the systemic circulation.

$C_{max}$ represents the maximum serum concentration obtained after drug administration and provides an indication that sufficient drug has reached the systemic circulation to provide a therapeutic response. In addition, $C_{max}$ provides warning of possible toxic drug levels.

$T_{max}$ was calculated and presented as median±range.

Pharmacokinetic Variables

For each subject, the following pharmacokinetic parameters were calculated, whenever possible, based on the serum concentrations of vitamin $B_{12}$ from Treatments A, B, and C, according to the model independent approach (Ref. 1):

$C_{max}$ Maximum observed concentration.

$t_{max}$ Time to maximum concentration.

$AUC_{0-t}$ Area under the concentration-time curve from time 0 to the time of last measurable concentration, calculated by the linear trapezoidal rule.

Pharmacokinetic calculations were performed, using SAS (SAS Inst., Version 8.02).

Statistical Methods Planned in the Protocol and Determination of Sample Size

Statistical and Analytical Plans

Pharmacokinetic Analysis

Levels of vitamin $B_{12}$ in serum samples were measured as pg/mL. Serum concentration values below the quantifiable limits of detection were treated as zero. Actual sampling times, rather than scheduled sampling times, were used in all computations of the pharmacokinetic parameters. For ease of presentation, however, scheduled sampling times were used to present results in tables, listings, and figures.

From the concentration data, non-compartmental pharmacokinetic parameters ($AUC_{0-t}$, $C_{max}$, $T_{max}$,) were calculated as described in Section 8.4.3.

Statistical Analysis

All statistical tests were conducted at the 0.05 significance level, unless otherwise specifically identified. Summary statistics of continuous parameters consisted of number (N), mean, median, SD, and range.

Descriptive statistics were obtained and tabulated by treatment for levels of vitamin $B_{12}$ at each time point and for the pharmacokinetic parameters calculated.

Bioequivalence was evaluated for the test (Treatment A—Nasal Spray) versus the reference (Treatment B—Gel). An analysis of variance (ANOVA, Ref. 2) was performed and the 90% confidence intervals were generated for the ratio of test/reference. $C_{max}$ and $AUC_{0-t}$ were natural log ($\log_e$) transformed prior to analysis. The corresponding 90% confidence intervals for the geometric mean ratio were obtained by taking the antilog of the 90% confidence intervals for the difference between the means on the log scale.

It was assumed that the test (Treatment A) is non-inferior (with respect to the reference (Treatment B) if the lower bound of the 90% confidence intervals from $\log_e$-transformed $C_{max}$, and $AUC_{0-t}$ were greater than or equal to 80%. If the lower bound of the 90% confidence intervals from $\log_e$-transformed $C_{max}$ and $AUC_{0-t}$ were less than 80%, it was assumed that non-inferiority could not be established.

The sequence effect was tested using the mean square error (MSE) for subject within sequence as the error term. All other main effects were tested against the MSE from the ANOVA model.

Bioavailability was evaluated for the test (Treatments A and B—Nasal Spray and Gel, respectively) and the reference (Treatment C—IM) groups. Relative bioavailability was assessed by examining the 90% confidence intervals for the ratio of the test (Treatments A and B) group means relative to the reference (Treatment C) group mean.

For $T_{max}$, the analyses were run using Wilcoxon's matched pairs method to determine if differences exist between the test group and each reference group.

SUMMARY—CONCLUSIONS

Pharmacokinetic Results:

The relative bioavailability for the two IN formulations was 0.9715. Bioavailability when comparing Treatment A (spray) versus Treatment C (IM) was 0.6105, and 0.6284 when comparing Treatment B (gel) versus Treatment C (IM).

The pharmacokinetic profiles of the spray formulation and the gel formulation were similar for $C_{max}$ (1480 pg/mL, 1670 pg/mL, respectively) and $AUC_{0-t}$ (92000 pg*hr/mL, 97000 pg*hr/mL, respectively). Additionally, the median difference for $T_{max}$ between the spray and gel IN formulation was less than 15 minutes (−0.24). The $C_{max}$ value for the IM formulation was significantly higher than the $C_{max}$ values for the two IN formulations ($p<0.0001$).

Bioequivalence was established for the Vitamin $B_{12}$ IN spray with regard to the gel data based on $C_{max}$ and $AUC_{0-t}$. The 90% confidence intervals for the $log_e$-transformed $C_{max}$ and $AUC_{0-t}$ for the spray and gel formulations fell within the range of 80% to 125%. Additionally, non-inferiority can be assumed when comparing the two IN formulations because the lower bounds of the confidence intervals are greater than 80% for both $AUC_{0-t}$ and $C_{max}$.

Conclusions:

The relative bioavailability for the two IN formulations was 0.9715. Bioavailability for Treatment A (spray) versus Treatment C (IM) was 0.6105, and 0.6284 when comparing Treatment B (gel) versus Treatment C (IM).

The pharmacokinetic profiles of the spray formulation and the gel formulation are similar for $C_{max}$ (1480 pg/mL, 1670 pg/mL, respectively) and $AUC_{0-t}$ (92000 pg*hr/mL, 97000 pg*hr/mL, respectively). Additionally, the median difference for $T_{max}$ between the spray and gel IN formulation was less than 15 minutes (−0.24). The $C_{max}$ value for the IM formulation was significantly higher than the $C_{max}$ values for the two IN formulations ($p<0.0001$).

Bioequivalence between the Vitamin $B_{12}$ spray formulation and the Vitamin $B_{12}$ gel formulation was established using $log_e$-transformed 90% confidence intervals for $AUC_{0-t}$ and $C_{max}$. The 90% confidence intervals for the $log_e$-transformed $C_{max}$ and $AUC_{0-t}$ for the spray and gel formulations fell within the range of 0.80 to 1.25. Noninferiority can be assumed for the two IN formulations (Treatment A versus Treatment B).

All Vitamin $B_{12}$ formulations were safe and well tolerated by healthy male and female volunteers.

EXAMPLE 2

We conducted a non-blinded, single dose, parallel group study to compare the uptake of Vitamin $B_{12}$ into the cerebrospinal fluid (CSF) after intranasal and intramuscular administration in healthy male and non-pregnant female volunteers. This study compared CSF levels to plasma levels produced by both formulations.

Thirty-six healthy male and non-pregnant female subjects, age 18 and over, were enrolled in the study. Eighteen subjects received a single intranasal dose of 500 mcg delivered as a 0.1 mL spray and eighteen subjects received a single intramuscular dose of 100 mcg delivered intramuscularly. Each subject visited the clinical site three times in a one-month period. These visits consisted of a screening visit, one dosing visit and a final visit.

After each dosing, each subject underwent lumbar puncture only once, with the retrieval of a total 4.0 mL of CSF (4 tubes, 1.0 mL per tube). One third of the subjects had a CSF sample collected at 60 minutes post dosing, one third of subjects had a CSF sample collected at 90 minutes post dosing, and one third of subjects had a CSF sample collected at 120 minutes post dosing In addition to the above, on the day of dosing 7 mL blood samples were drawn before dosing and post dosing at 5, 10, 15 and 20 minutes, and at 0.5, 1, 1½, 2, 3, 4, 6, and 8 hours post-dose (prior to discharge).

The cerebrospinal fluid was evaluated for total Vitamin B12 content. It was the objective of the study described herein to measure the amount of Vitamin $B_{12}$ present in the blood and CSF following intramuscular (IM) and nasal administration.

Reference and Test Products

Reference Product: Cyanocobalamin 100 mcg intramuscular injection.

Cyanocobalamin Injection, USP is a sterile solution of cyanocobalamin (Vitamin B12) for intramuscular or subcutaneous injection. Each mL contains 1,000 mcg cyanocobalamin.

Test Product: Vitamin B12 Nasal Spray=500 mcg/0.1 mL spray. The cyanocobalamin intranasal aqueous solution was a preferred formulation of the present invention and contained cyanocobalamin at a concentration of 0.5% (percent of total weight), citric acid 0.12%, sodium citrate 0.32%, glycerin 2.23%, 50% benzalkonium chloride solution 0.04% and 96.79% water.

Vitamin B12 Nasal Spray is supplied as a 2.3 mL bottle to deliver one dose: 500 mcg/0.1 mL per dose.

Before intranasal dosing, all subjects were be given an orientation of the proper dosing technique and general conduct of the study.

The subject was instructed to gently blow his/her nose. The subject remained in a seated position, and the primed IN applicator was inserted into the nostril by the subject, under the direction of the study staff. During dosing, the contralateral nostril was closed with the forefinger. Subjects will also be instructed to tilt their heads slightly back for dosing and to return their heads to an upright position while sniffing in gently immediately following dosing. A 0.1 mL dose of vitamin B12 spray will be released into the nasal cavity. (A dose is a single application to one nostril.) Subjects must inform the staff if they sneeze or if the product drips out of their nose. Subjects will not be re-dosed if they sneeze or if the product drips out of their nose. Subjects will be instructed to refrain from blowing their nose for 1 hour following IN treatment.

After dosing, each subject underwent lumbar puncture, involving the retrieval of 4.0 mL of CSF (4 tubes, 1.0 mL per tube). One third of subjects from each group will have a CSF sample collected at 60 minutes post dosing, one third of subjects will have a CSF sample collected at 90 minutes post dosing, and one third of subjects will have a CSF sample collected at 120 minutes post dosing.

At the appropriate time after dosing, the Investigator positioned the patient appropriately in order to proceed with lumbar puncture. The lumbar area was prepared and draped in the usual aseptic fashion. Local anesthesia was utilized (1% xylocaine, 1-5 mL). Upon reaching a state of adequate anesthesia, a spinal needle (20 or 22G) was introduced into the spinal canal, at the level deemed appropriate by the Investigator. The CSF samples were collected 60, 90 or 120 minutes after administration. A total of 4.0 mL of CSF were collected from each patient, and distributed into 4 separate collection tubes. The tubes were appropriately labeled with a patient identifier and submitted for bioanalytical analysis. Upon completion of CSF collection, the spinal needle was removed.

The levels of vitamin B12 were determined in both the CSF and blood serum using Vitamin $B_{12}$ concentrations in the CSF will be analyzed for Qualitative determination of Vitamin $B_{12}$ using a validated TOSOH Nex. 1A procedure.

RESULTS AND CONCLUSION

The data showed that the ration of vitamin B12 to serum was higher in those individuals receiving intranasal administration of vitamin B12 than those receiving intramuscular injections of vitamin B12.

The average ratio (B12 CSF/B12 Serum×100) ranged from 1.1 to 1.9 for those individuals receiving intranasal administration of vitamin B12 while those who received intramuscular injections of vitamin B12 had an average ratio ranging from 0.17 to 0.24. This is a surprising result in that intranasal administration only has about a 7-12% bioavailability in the blood serum relative to intramuscular injection of vitamin B12. This indicates that intranasal administration of vitamin B12 reaches the CSF much more effectively than by intramuscular injection.

EXAMPLE 3

Production of a Cyanocobalamin Solution

A 4000 g batch of a cyanocobalamin solution of the present invention, which had a concentration of 500 mcg/0.1 g of solution.

Starting Materials
I. Formula Record

| Ingredient Name | Theoretical Weight (Grams) |
|---|---|
| Cyanocobalamin, USP | 20.0 |
| Citric Acid, USP (Anhydrous) | 4.8 |
| Sodium Citrate, USP (Dihydrate) | 12.8 |
| Glycerin, USP | 89.2 |
| Benzalkonium Chloride Solution, NF (50%) | 1.6 |
| Purified Water, USP | 3871.6* |

The 3871.6 grams of water was placed in a stainless steel container, which had been placed on a hot plate. The water was heated to about 30° C. and stirred. Into the heated water was added 12.8 g of sodium citrate while the water was being stirred at 300 rpm for 5 minutes. The 4.8 g of citric acid was then added and stirred for 10 minutes. Into this mixture was added 20.0 g of cyanocobalamin and stirred for 30 minutes at 30° C. at 300 rpm. The hot plate was then turned off. The 89.2 g of glycerin was added and stirred for 5 minutes at 300 rpm. Into the cyanocobalamin solution was then added 1.6 g of an aqueous solution containing 50% by weight of Benzalkonium Chloride was added to the solution and stirred for 5 minutes at 300 rpm. The pH was then measured and adjusted if the pH was not with the 4.5-5.5 range. Additional water was added to bring the weight of the solution to 4000 g.

What is claimed is:

1. A stable pharmaceutical aqueous solution of cyanocobalamin comprised of cyanocobalamin and water, a preservative selected from the group consisting of benzyl alcohol, parabens thimerosal, chlorobutanol, benzethonium chloride, and benzalkonium chloride, and combinations thereof, a buffer selected from the group consisting of citric acid, sodium citrate, monopotassium phosphate, disodium phosphate, potassium biphthalate, sodium hydroxide, sodium acetate, acetic acid, and combinations thereof, and a humectant selected from the group consisting of sorbitol, propylene glycol, and glycerin, and combinations thereof, wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin with the proviso that the solution contains no mercury or mercury compounds.

2. The aqueous solution of cyanocobalamin of claim 1, wherein the solution is comprised of citric acid, and sodium citrate and water and has a pH of about 4-6.

3. The aqueous solution of claim 2 wherein the pH of the solution is about 5.

4. The aqueous solution of claim 2 further comprised of claim 1 wherein the humectant is propylene glycol.

5. The aqueous solution of claim 1 wherein the humectant is sorbitol.

6. The aqueous solution of claim 1 wherein the humectant is glycerin.

7. The aqueous solution of claim 6 wherein the glycerin is present at a concentration of about 2.23%.

8. The aqueous solution of claim 2 wherein the preservative is selected from the group consisting of benzyl alcohol, chlorobutanol and benzalkonium chloride.

9. The aqueous solution of claim 8 wherein the preservative includes chlorobutanol.

10. The aqueous solution of claim 9 wherein the preservative includes benzalkonium chloride.

11. The aqueous solution of claim 10 wherein the benzalkonium chloride is present in solution at a concentration of about 0.02%.

12. The aqueous solution of claim 2 wherein cyanocobalamin is present at about concentration 0.5% percent of total weight, citric acid is present at a concentration of about 0.12%, and sodium citrate is present at a concentration of about 0.32%.

13. The aqueous solution of claim 12 wherein the pH of the solution is about 5.

14. The aqueous solution of claim 12 wherein the humectant includes sorbital.

15. The aqueous solution of claim 14 wherein the humectant includes propylene glycol.

16. The aqueous solution of claim 15 wherein the humectant includes glycerin.

17. The aqueous solution of claim 16 wherein glycerin is present in solution at a concentration of about 2.23%.

18. The aqueous solution of claim 12 wherein the preservative is selected from the group consisting of benzyl alcohol chlorobutanol and benzalkonium chloride.

19. The aqueous solution of claim 18 wherein the preservative includes chlorobutanol.

20. The aqueous solution of claim 19 wherein the preservative includes benzalkonium chloride.

21. The aqueous solution of claim 20 wherein the benzalkonium chloride is present in solution at a concentration of about 0.02%.

22. The aqueous solution of claim 1 wherein the solution of cyanocobalamin has at least about 12% bioavailability relative to an intramuscular injection of cyanocobalamin.

23. A stable pharmaceutical aqueous solution of cyanocobalamin comprised of cyanocobalamin at a concentration of about 0.5% of total weight of solution, citric acid at a concentration of about 0.12%, sodium citrate at a concentration of about 0.32%, glycerin at a concentration of about 2.23%, benzalkonium chloride at concentration of about 0.02% and water wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin with the proviso that mercury and mercury containing compounds are not present.

24. A method for administering cyanocobalamin comprised of infusing the nose with an aqueous solution of cyanocobalamin, wherein the solution of cyanocobalamin comprises a preservative selected from the group consisting of benzyl alcohol, parabens thimerosal, chlorobutanol, benzethonium chloride, and benzalkonium chloride, and combinations thereof, a buffer selected from the group consisting of citric acid, sodium citrate, monopotassium phosphate, disodium phosphate, potassium biphthalate, sodium hydroxide, sodium acetate, and acetic acid, combinations thereof, and a humectant selected from the group consisting of sorbitol, propylene glycol, and glycerin, and combinations thereof, and has a viscosity of less than 1000 cPs, and wherein said solution of cyanocobalamin has a bioavailability of cyanocobalamin of about 7% relative to an intramuscular injection of cyanocobalamin, with the proviso that mercury and mercury containing compounds are not present in the solution.

25. The method of claim 24 wherein the buffer includes citric acid and sodium citrate wherein the solution has a pH of from about 4-6.

26. The method of claim 25 wherein the pH of the solution is about 5.

27. The method of claim 25 wherein cyanocobalamin is present in solution at a concentration of between 0.5-1% by weight.

28. The method of claim 27 wherein the concentration of cyanocobalamin in solution is about 0.5%.

29. The method of claim 25 wherein the citric acid is present in solution at a concentration of about 0.12%, and the sodium citrate is present in solution at a concentration of about 0.32%, in water.

30. A method for administering cyanocobalamin comprised of infusing the nose with an aqueous solution of cyanocobalamin wherein said aqueous solution of cyanocobalamin is comprised of cyanocobalamin at a concentration of about 0.5% of total weight of solution, citric acid at a concentration of about 0.12%, sodium citrate at a concentration of about 0.32%, glycerin at a concentration of about 2.23%, benzalkonium chloride at concentration of about 0.02% and water wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin, with the proviso that the solution of cyanocobalamin contains no mercury or mercury-containing compounds.

31. A method for elevating the vitamin B12 levels in the cerebral spinal fluid (CSF) comprising administering intranasally a sufficient amount of a solution of cyanocobalamin so that the average ratio of vitamin B12 in the CSF to that in the blood serum (B12 CSF/B12 Serum×100) is increased to at least about 1.1, wherein said aqueous solution of cyanocobalamin is comprised of cyanocobalamin at a concentration of about 0.5% of total weight of solution, citric acid at a concentration of about 0.12%, sodium citrate at a concentration of about 0.32%, glycerin at a concentration of about 2.23%, benzalkonium chloride at concentration of about 0.02% and water wherein said solution of cyanocobalamin is suitable for intranasal administration, has a viscosity less than about 1000 cPs, and wherein said solution of cyanocobalamin has a bioavailability of cyanocobalamin when administered intranasally of at least about 7% relative to an intramuscular injection of cyanocobalamin, with the proviso that the cyanocobalamin solution contains no mercury or mercury-containing compounds.

* * * * *